United States Patent [19]

Sturm et al.

[11] 3,969,367
[45] July 13, 1976

[54] OCTAHYDROINDOLE PHOSPHORYLACYLAMINES

[75] Inventors: Elmar Sturm, Aesch, Switzerland; Hans Jörg Cellarius, deceased, late of Riehen, Switzerland, by Herta Cellarius-Haigermoser, legal representative

[73] Assignee: Ciba-Geigy Corporation, Ardsley, N.Y.

[22] Filed: Jan. 30, 1975

[21] Appl. No.: 545,465

Related U.S. Application Data

[62] Division of Ser. No. 324,469, Jan. 17, 1973, Pat. No. 3,876,643.

[30] Foreign Application Priority Data

Jan. 20, 1972  Switzerland.......................... 910/72

[52] U.S. Cl............................................ 260/326.12 R
[51] Int. Cl.²........................................ C07D 209/12
[58] Field of Search ........................... 260/326.12 R

[56] References Cited
UNITED STATES PATENTS

| | | | |
|---|---|---|---|
| 3,347,850 | 10/1967 | Baker et al. ....................... | 260/239 |
| 3,371,095 | 2/1968 | Lorenz et al..................... | 260/294.8 |
| 3,501,461 | 3/1970 | Newallis et al. .................... | 260/239 |

*Primary Examiner*—Lewis Gotts
*Assistant Examiner*—S. P. Williams
*Attorney, Agent, or Firm*—Frederick H. Rabin

[57] ABSTRACT

Phosphorylthio-acetyl derivatives of decahydroquinolines, octahydroindoles and octahydropyrindines are effective plant regulating agents (growth regulators and selective herbicides) and fungicides.

The new phosphorylacylamines correspond to the formula I

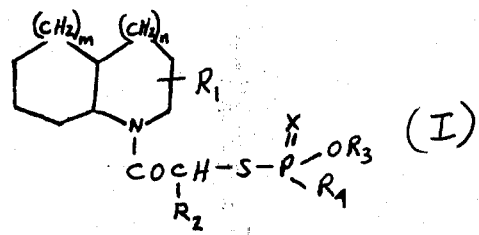

wherein $R_1$ and $R_2$ each independently represents hydrogen or methyl, $R_3$ represents alkyl or haloalkyl, $R_4$ represents alkyl, alkoxy, haloalkoxy, alkylthio or an amino radical, X represents oxygen or sulphur, and one of the two indices $m$ and $n$ represents 1 and the other represents 0 or 1.

5 Claims, No Drawings

OCTAHYDROINDOLE PHOSPHORYLACYLAMINES

This is a division of application Ser. No. 324,469 filed on Jan. 17, 1973, now U.S. Pat. No. 3,876,643.

The present invention relates to phosphoryl-acylamines, a process for their manufacture, also to agents which contain these new compounds as plant regulating and fungicidal active substances, as well as to a method of combating weeds and phytopathogenic fungi and to a method of regulating the growth of useful plants which comprises the use of the new active substances or of agents which contain them.

The new phosphorylacylamines correspond to the formula I

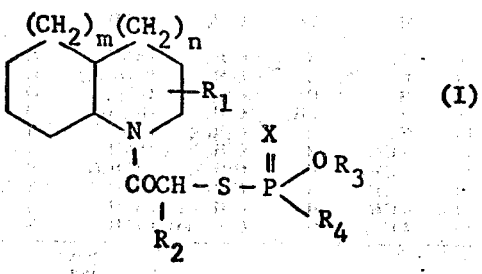

wherein $R_1$ and $R_2$ each independently represents hydrogen or methyl, $R_3$ represents alkyl or haloalkyl, $R_4$ represents alkyl, alkoxy, haloalkoxy, alkylthio or an amino radical, X represents oxygen or sulphur, and one of the two indices $m$ and $n$ represents 1 and the other represents 0 or 1.

By alkyl radicals $R_3$ and $R_4$ are meant straight-chain or branched radicals with 1 to 4 carbon atoms, such as the methyl, ethyl, n-propyl, isopropyl, n-butyl, isobutyl, sec.- or tert. butyl radical. Such alkyl radicals also for the alkyl moiety of haloalkyl radicals $R_3$ and of alkoxy, haloalkoxy or alkylthio radicals $R_4$. Halogen as substituents of an haloalkyl or haloalkoxy radical can be fluorine, chlorine, bromine or iodine, in particular chlorine or bromine.

The new phosphoric esters of the formula I are obtained according to the present invention by converting a heterocycle of the formula II

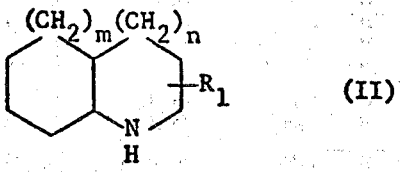

with a halogenated acylating agent into compounds of the formula III

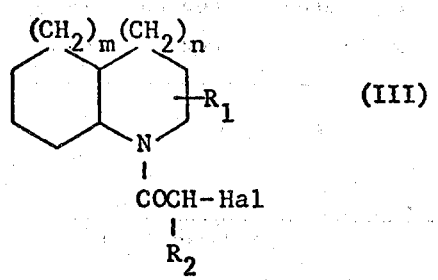

and subsequently reacting these either in the presence of an acid binding agent with a phosphoric ester of the formula IV

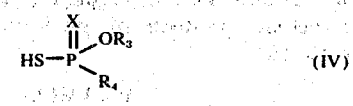

or with an alkali salt or an ammonium salt of such a phosphoric ester.

In the formulae II to IV $R_1$, $R_2$, $R_3$, $R_4$, X, $m$ and $n$ have the meanings given under the formula I, Hal in formula III represents a halogen atom, preferably chlorine or bromine.

The reactions are carried out in the presence of solvents or diluents which are inert towards the reactants. The following solvents or diluents can be used for example: aliphatic, aromatic or halogenated hydrocarbons, such as benzene, toluene, xylene, chlorobenzene, methylene chloride, chloroform; ethers and ethereal compounds, such as dialkyl ether, dioxan, tetrahydrofuran; ketones, such as acetone, methyl ethyl ketone; nitriles, such as acetonitrile; N,N-dialkylated amides, such as dimethyl formamide; also dimethyl sulphoxide, as well as mixtures of these solvents with one another.

As halogenated acylating agents there are used preferably halogenated alkanecarboxylic acid halides, such as chloroacetyl chloride or α-chloropropionyl chloride. However, it is also possible to carry out the reaction with halogenated alkanecarboxylic acid anhydrides, e.g. chloroacetic anhydride. When using halogenated alkanecarboxylic acid halides the haloacylation is carried out in the presence of an acid binding agent. Suitable acid binding agents are: tertiary amines, such as trialkylamines, e.g. triethylamine, pyridine and pyridine bases, or inorganic bases, such as the oxides, hydroxides, hydrogen carbonates and carbonates of alkali and alkaline earth metals. It is also possible to use as acid binding agent the respective reactant of the formula II, which in this case must be used in excess. The compounds of the formula II obtained by these reactions have hitherto not been described.

The reaction temperatures are between 0° and 100°C, preferably between 0° and 60°C.

The compounds encompassed by formula I can be in two isomeric forms, namely in the cis- and trans-configuration. The following connexions apply:

a. octahydropyrindene is in the cis-form by virtue of its ring synthesis. Accordingly, the compounds of the formula I derived therefrom are also in the cis-form.

b. Octahydroindole derivatives of the formula I are mixtures of the cis- and trans-form.

c. Decahydroquinoline can be manufactured as pure cis- or trans-form. Accordingly, the compounds of the formula I derived therefrom are also in the cis- or trans-form. However, in practice the stereospecific decahydroquinoline used as starting product will also contain a slight amount of the other isomer. But this does not as a rule impair the activity spectrum of the desired isomer.

d. Decahydroquinaldine derivatives of the formula I are mixtures of the cis- and trans-form.

The following Example will serve to illustrate the process according to the invention. In the accompanying Tables (a), (b) and (c) there are summarised further compounds of the formula I which were obtained by the process described in the Example, or by one of the variants thereof mentioned hereinbefore; new intermediate products of the formula III are listed in Table (d).

EXAMPLE a. A solution of 20 g of trans-decahydroquinoline in 150 ml of diethyl ether is treated with a solution of 5.75 g of sodium hydroxide in 150 ml of water. While stirring vigorously, 16.3 g of chloroacetyl chloride are added dropwise at 0°–10°C and the reaction mixture is further stirred for 2 hours at room temperature. The organic phase is then isolated, washed neutral with water, dried, and the solvent evaporated in vacuo. The residual oil is distilled in a high vacuum to give 26 g of 1-chloroacetyl-trans-decahydroquinoline as a colourless oil with a boiling point of 104–108°C/0.05 Torr.

b. To a solution of 11 g of 1-chloroacetyl-trans-decahydro-quinoline in 100 ml of acetone is added a solution of 10 g of the potassium salt of O,O-dimethyldithiophosphoric acid in 100 ml of acetone and the mixture is allowed to stand for 24 hours at 25°C. The precipitated potassium chloride is filtered off and the solvent distilled in vacuo to leave as residue 15 g of 1-(O,O-dimethyl-thiophosphorylthio-acetyl)-trans-decahydroquinoline as a yellow oil; $n_D^{20} = 1.5515$. [Compound 45]. The following phosphoric esters encompassed by the formula I were obtained in the way described in the preceding Example:

Table a

Octahydropyrindine derivatives

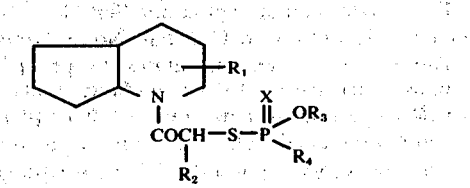

| Comp. No. | $R_1$ | $R_2$ | $R_3$ | $R_4$ | X | $n_D^{20}$ |
|---|---|---|---|---|---|---|
| 1 | H | H | $CH_3$ | $OCH_3$ | S | 1.5502 |
| 2 | H | H | $C_2H_5$ | $OC_2H_5$ | S | 1.5465 |
| 3 | H | H | $C_3H_7$(iso) | $OC_3H_7$(iso) | S | 1.5340 |
| 4 | H | H | $C_3H_7$(n) | $OC_3H_7$(n) | S | 1.5375 $n_D^{24}=$ |
| 5 | H | $CH_3$ | $C_2H_5$ | $OC_2H_5$ | S | 1.5366 $n_D^{24}=$ |
| 6 | H | H | $C_2H_5$ | $OC_2H_5$ | O | 1.5175 |
| 7 | H | H | $C_2H_5$ | $SC_3H_7$(n) | O | viscos |
| 8 | H | H | $CH_3$ | $OCH_3$ | O | viscos |
| 9 | H | $CH_3$ | $C_2H_5$ | $OC_2H_5$ | O | Oel |
| 10 | H | H | $C_2H_5$ | $CH_3$ | S | Oel |
| 11 | 3-$CH_3$ | H | $C_2H_5$ | $OC_2H_5$ | S | 1.5372 |
| 12 | 3-$CH_3$ | H | $C_3H_7$(n) | $OC_3H_7$(n) | S | 1.5318 |
| 13 | 4-$CH_3$ | H | $C_2H_5$ | $OC_2H_5$ | S | 1.5416 |
| 14 | 4-$CH_3$ | H | $C_3H_7$(n) | $OC_3H_7$(n) | S | 1.5354 |
| 15 | 4-$CH_3$ | H | $C_3H_7$(iso) | $OC_3H_7$(iso) | S | 1.5299 |

Table b

Decahydroquinoline derivatives

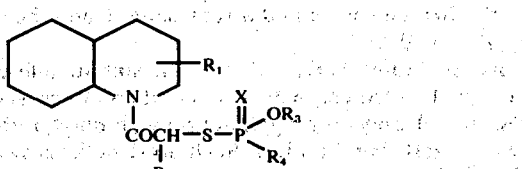

| Comp. No. | $R_1$ | $R_2$ | $R_3$ | $R_4$ | X | configuration | $n_D^{20}$ |
|---|---|---|---|---|---|---|---|
| 16 | H | H | $C_2H_5$ | $OC_2H_5$ | S | trans | 1.5435 |
| 17 | H | H | $C_3H_7$(iso) | $OC_3H_7$(iso) | S | trans | 1.5289 |
| 18 | H | H | $C_3H_7$(n) | $OC_3H_7$(n) | S | trans | 1.5354 $n_D^{24}=$ |
| 19 | H | H | $C_2H_5$ | $OC_2H_5$ | O | trans | 1.5685 |
| 20 | H | H | $CH_2CH_2Cl$ | $OCH_2CH_2Cl$ | O | trans | oil |
| 21 | H | H | $C_2H_5$ | $OC_4H_9$(sec) | O | trans | oil |
| 22 | H | H | $CH_3$ | $OCH_3$ | S | cis | 1.5530 |
| 23 | H | H | $C_2H_5$ | $OC_2H_5$ | S | cis | 1.5454 |
| 24 | H | H | $C_3H_7$(iso) | $OC_3H_7$(iso) | S | cis | 1.5332 |
| 25 | H | H | $C_3H_7$(n) | $OC_3H_7$(n) | S | cis | 1.5300 $n_D^{24}=$ |
| 26 | H | $CH_3$ | $C_2H_5$ | $OC_2H_5$ | S | cis | 1.5349 |
| 27 | H | H | $C_2H_5$ | $OC_2H_5$ | O | cis | $n_D^{24}=$ 1.5175 |
| 28 | H | H | $C_2H_5$ | $SC_3H_7$(n) | O | cis | oil |
| 29 | H | H | $C_2H_5$ | $NH_2$ | O | cis | viscous |
| 30 | H | H | $CH_3$ | $OCH_3$ | O | trans | oil |
| 31 | H | H | $CH_3$ | $OCH_3$ | O | cis | oil |
| 32 | H | H | $CH_3$ | $OC_4H_9$(n) | O | cis | oil |
| 33 | 2-$CH_3$ | H | $C_2H_5$ | $OC_2H_5$ | S | cis/trans | 1.5436 |
| 34 | 2-$CH_3$ | H | $C_3H_7$(n) | $OC_3H_7$(n) | S | cis/trans | 1.5339 |
| 35 | 2-$CH_3$ | H | $C_2H_5$ | $OC_2H_5$ | O | cis/trans | oil |

Table c

Octahydroindole derivatives

Table c-continued

Octahydroindole derivatives

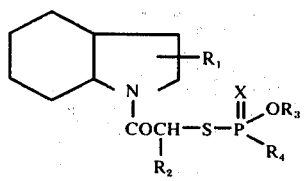

| Comp. No. | $R_1$ | $R_2$ | $R_3$ | $R_4$ | X | $n_D^{20}$ |
|---|---|---|---|---|---|---|
| 36 | H | H | $C_2H_5$ | $OC_2H_5$ | S | 1.5458 |
| 37 | H | H | $C_3H_7(n)$ | $OC_3H_7(n)$ | S | 1.5365 |
| 38 | H | H | $C_3H_7(iso)$ | $OC_3H_7(iso)$ | S | 1.5318 |
| 39 | H | H | $CH_3$ | $OCH_3$ | O | oil |
| 40 | 2-$CH_3$ | H | $CH_3$ | $OCH_3$ | S | 1.5483 |
| 41 | 2-$CH_3$ | H | $C_2H_5$ | $OC_2H_5$ | S | 1.5380 |
| 42 | 2-$CH_3$ | H | $C_3H_7(n)$ | $OC_3H_7(n)$ | S | 1.5368 |
| 43 | 2-$CH_3$ | H | $C_3H_7(iso)$ | $OC_3H_7(iso)$ | S | 1.5267 |
| 44 | 2-$CH_3$ | H | $C_2H_5$ | $OC_2H_5$ | O | wax |

Table d

| Compound | Intermediate products of the formula III | Physical Data |
|---|---|---|
| 1-chloroacetyl-cis-decahydroquinoline | m.p.: | 88°–90°C |
| 1-chloroacetyl-2-methyl-decahydroquinoline | $n_D^{20}=$ | 1,5175 |
| 1-chloroacetyl-octahydro-1H-indole | b.p.: | 112°–118° 0,03 Torr |
| 1-chloroacetyl-2-methyl-octahydro-1H-indole | b.p.: | 106°–110° 0,04 Torr |
| 1-chloroacetyl-octahydro-1H-1-pyridine | b.p.: | 104°–107° 0,1 Torr |
| 1-chloroacetyl-3-methyl-octahydro-1H-1-pyrindine | b.p.: | 115°/ 0,17 Torr |
| 1-chloroacetyl-4-methyl-octahydro-1H-1-pyrindine | $n_D^{20}=$ | 1,5180 |
| 1-α-chloropropionyl-cis-decahydroquinoline | $n_D^{20}=$ | 1,5154 |
| 1-α-chloropropionyl-octahydro-1H-1-pyrindine | $n_D^{20}=$ | 1,5165 |

The active substances according to the invention have very good plant regulating properties. As herbicides they have very good action against Panicum type plants such as Setaria sp. and Digitaria sp. and against grasses, such as Lolium sp., Alopecurus sp. and Poa sp., without causing damage to cultivated plants, for example such as soya beans, cotton, sugar beet, maize or cereals.

Furthermore, difficultly combattable weeds in rice cultures (cultures of dry and water rice), such as Echinochloa sp., are attacked and destroyed by these active substances. Since the active substances are nontoxic in conventional rates of application and do not upset the balance of nature, they are highly suitable for application in cultures of water rice. However, they can also be used for the important task of combatting weeds in areas of land surrounding the rice cultures, such as ditches, canal beds, embankments etc.

The active substances are applied before and after germination of the plants (pre- and postemergence).

The regulation of useful plants with the compounds of the formula I primarily takes the form of a uniform or partial growth inhibition. Cotton, soya or cereals flourish as plants of diminished size and reduced internodal intervals without any accompanying decrease in the harvest yield. The stability of the plants is improved and the tendency to break (to lie flat) induced by high winds, thunderstorms, or hailstorms, is substantially reduced. The partial growth inhibition is to be understood both in the sense of time of growth and location in the plant.

It is possible to prevent the growth of undesirable shoots, e.g. in tobacco plants or ornamental plants. A decrease in growth occurs in grasses.

In addition, the compounds of the formula I also display effects which impinge directly on the process of improvement of the harvest yield.

Moreover, the compounds of the formula I possess excellent fugicidal properties against phytopathogenic fungi. Fungus infections occuring on fruit, blossoms, leaves, stems and roots can be checked or destroyed with the new active substances and parts of plants which grow later remain protected from such infections. The new active substances have extraordinarily good activity against Pirisularia species, such as Piricularia oryzae and mildew fungus species, such as Erysiphe zucchetti.

On account of their good herbicidal and fungicidal properties interest attaches to phosphoric esters of the formula Ia

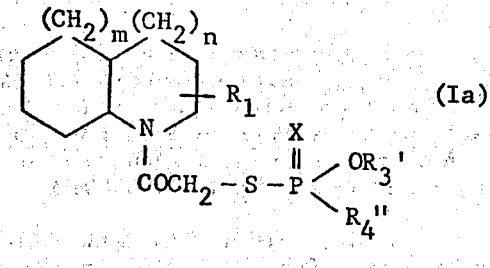

wherein $R_1$, X, m and n have the meanings given under the formula I, $R_1'$ represents an alkyl radical with 1 to 3 carbon atoms and $R_4''$ represents an alkoxy radical with 1 to 3 carbon atoms.

The intermediate products of the formula III possess good herbicidal properties.

The herbicidal action of the compounds according to the invention was determined in the light of the following tests:

1. Herbicidal action on preemergence application

Immediately after the test plants have been sown, the active substances are applied to the surface of the soil as an aqueous dispersion (obtained from a 25% wettable powder). The seed dishes are then kept at 22°–25°C relative humidity. The test is evaluated after 28 days.

The test plants used were:
Cultivated plants:
 soya beans (Glycine hyspida)
 cotton (Gossypium herbaccara)
 sugar beet (beta vulgaris)
Weeds:
 Digitaria sanguinale
 Setaria italica
 Alopecurus myosuroides
 Lolium multiflorum
 Poa trivialis The respective rates of application are to be found in the following Table. Evaluation is according to the following rating:
 9 = plants undamaged (control)
 1 = plants destroyed
 2–8 = intermediate stages of damage

| Compound No. | Rate of application in kg/ha | Digitaria sanguinale | Setaria italica | Alopecurus myosuroides | Lolium multiflorum | Poa trivalis |
|---|---|---|---|---|---|---|
| 16 | 4 | 1 | 1 | 1 | 1 | 1 |
|  | 2 | 1 | 3 | 2 | 2 | 1 |
|  | 1 | 3 | 3 | 3 | 3 | 1 |
| 2 | 4 | 1 | 1 | 1 | 1 |  |
|  | 2 | 1 | 2 | 1 | 3 |  |
|  | 1 | 3 | 3 | 3 | 4 |  |
| 23 | 4 | 1 | 1 | 2 | 1 |  |
|  | 2 | 2 | 2 | 2 | 2 |  |
|  | 1 | 2 | 4 | 3 | 3 |  |
| 1 | 4 | 1 | 1 |  | 2 | 1 |
|  | 2 | 1 | 1 |  | 3 | 1 |
|  | 1 | — | 3 |  | — | 1 |
| 22 | 4 | 2 | 1 |  |  |  |
|  | 2 | 2 | 1 |  |  |  |
|  | 1 | 3 | 3 |  |  |  |

The cited cultivated plants, soya beans, cotton and sugar beet, as well as cereals (wheat and oats), are neither damaged nor hindered in their growth by the active substances listed hereinabove.

2. Preemergence test in rice in which weeds have been sown a. Dry test

In pots filled with garden soil are sown as test plant rice (*Oryza Oryzoides*) and as weed *Echinochloa crus galli*. The active substance is processed to a 25% wettable powder and is applied to the surface of the soil in the form of an aqueous dispersion immediately after the sowing (amount of broth: 100 ml /m$^2$).

b. Wet test

The aqueous dispersion of the active substance is applied to the surface of the test pots and worked in to a depth of about 1 cm. Then the test plants (rice and *Echinochloa crus galli*) are sown and the soil is completely saturated with water. Upon emergence of the seed, the water level in the pots is brought to about 2-3 cm above the surface of the soil.

Both tests are carried out in a greenhouse at 24°–27°C and 70% relative humidity. The evaluation is carried out 28 days later according to the rating given in Test 1.

| Compound No. | Rate of application in kg/ha | Dry test | | Wet test | |
|---|---|---|---|---|---|
|  |  | Echinochloa crus galli | Rice | Echinochloa crus galli | Rice |
| 22 | 4 | 1 | 8 | 2 | 8 |
|  | 2 | 1 | 8 | 2 | 8 |
| 16 | 4 | 1 | 9 | 2 | 8 |
|  | 2 | 1 | 9 | 2 | 9 |
| 23 | 4 | 2 | 8 | 2 | 8 |
|  | 2 | 2 | 8 | 2 | 8 |
| 1 | 4 | 2 | 8 | — | — |
|  | 2 | 2 | 9 | — | — |

3. Inhibition of side-shoot formation in tobacco

Tobacco plants of the variety "Sota 27" were cultivated in the open in accordance with practice. One month before harvesting (22nd, August) the inflorescences were pruned. All the plants were then sprayed dripping wet with a specific active substance concentration for each 5 m$^2$ area. During the harvesting on 20th. September, the weight of side-shoots of all plants determined per plot was assessed in proportion to the number of plants. The average weight of side-shoots per plant was ascertained therefrom. In the same way the average number of side-shoots per plant was determined. The following results were obtained:

| Compound No. | Rate of application of active Substance | Weight of side-shoots per plant | Number of side-shoots per plant |
|---|---|---|---|
| 25 | 10 kg/ha | 30 g | 1,7 |
|  | 5 kg/ha | 70 g | 4,9 |
| 4 | 10 kg/ha | 55 g | 2,5 |
|  | 5 kg/ha | 55 g | 2,4 |
| untreated control | — | 225 g | 7,0 |

4. Inhibition of growth in length in cereals

Very thickly sown summer barley of the variety "Union" was sprayed with an active substance solution at the end of the tillering period on 10th. May. A plot having an area of 3 m$^2$ was allotted to each active substance concentration. Evaluation took place on 17th. July shortly before harvesting and comprised the height of the plants and the degree to which they lay flat induced by the density of sowing (= stalks lying flat).

| Compound No. | Rate of application of active Substance | Height of the plants (average) | Degree to which plants lie flat |
|---|---|---|---|
| 25 | 4 kg/ha | 85 cm | — |
|  | 2 kg/ha | 105 cm | + |
| 4 | 4 kg/ha | 75 cm | — |
|  | 2 kg/ha | 100 cm | — |
| control | — | 115 cm | + + |

Explanation:
+ + = lying very flat
+ = lying flat
— = plants standing upright

The fungicidal action of the compounds according to the invention was determined by the following test:

Action against *Piricularia oryzae*

Rice plants are cultivated in a greenhouse and in the 1–2 leaf stage are sprayed with an aqueous spray broth which contains 0.05% of the respective active substance. Two days later the plants are infected with an aqueous conidia suspension of Piricularia oryzae and incubated in a humid chamber at 27°C. The test is evaluated after 6 days.

The plants treated with compounds
no.'s 2,14 — Table (a)
no. 17 — Table (b)
no.'s 38,41,42 — Table (c)
showed no attack by fungus, whereas the untreated plants were 100% attacked.

The agents according to the invention are manufactured in known manner by intimately mixing and/or grinding active substances of the formula I with the suitable carriers, optionally with the addition of dispersants or solvents which are inert towards the active substances. The active substances may take and be used in the following forms:

Solid forms:
dusts, tracking agents, granules, coated granules, impregnated granules and homogeneous granules.

Liquid forms:
a. active substances which are dispersible in water: wettable powders, pastes, emulsions;
b. solutions.

To manufacture solide forms ) dusts, tracking agents), the active substances are mixed with solid carriers. Suitable carriers are, for example: kaolin, talcum, bolus, loess, chalk, limestone, ground limestone, attaclay, dolomite, diatomaceous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc. These substances can either be used singly or in admixture with one another.

The particle size of the carriers for dusts is advantageously up to 0.1 mm, for tracking agents from about 0.075 to 0.2 mm, and for granules 0.2 mm or larger.

The solid forms contain the active substances in concentrations from 0.5 to 80%.

To these mixtures can also be added additives which stabilize the active substance and/or non-ionic, anionic and cationic surface active substances, which for example improve the adhesion of the active ingredients on plants or parts of plants (adhesives and agglutinants) and/or ensure a better wettability (wetting agents) and dispersibility (dispersing agents). Examples of suitable adhesives are the following: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulphonic acids, their alkali metal and alkaline earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of urea and formaldehyde, and also latex products. Preferred dispersions (suspensions and emulsions) are manufactured by mixing or grinding the active substance with carriers accompanied by the addition of dispersing agents and solvents, in the process of which there result firstly dispersible active substance concentrations, such as wettable powders and emulsifiable concentrates.

The water-dispersible concentrates of the active substance i.e. wettable powders, pastes and emulsifiable concentrates are agents which can be diluted with water to any concentration desired. They consist of active substance, carrier, optionally additives which stabilize the active substance, surface-active substances and anti-foam agents and, optionally, solvents. The active substance concentrations in these agents are from 5–80%.

Wettable powders and pastes are obtained by mixing and grinding the active substances with dispersing agents and pulverulent carriers in suitable apparatus until homogeneity is attained. Carriers are, for example, those mentioned for the solid forms of application. In some cases it is advantageous to use mixtures of different carriers. As dispersing agents there can be used, for example, condensation products of sulphonated naphthalene and sulphonated naphthalene derivatives with formaldehyde, condensation products of naphthalene or naphthalene sulphonic acids with phenol and formaldehyde, as well as alkali, ammonium and alkaline earth metal salts of lignin sulphonic acid, in addition, alkylaryl suphonates, alkali and alkaline earth metal salts of dibutyl naphthalene sulphonic acid, fatty alcohol sulphates such as salts of sulphated hexadecanols, heptadecanols, octadecanols, and salts of sulphated fatty alcohol glycol ethers, the sodium salt of oleoyl ethionate, the sodium salt of olcoyl methyl tauride, ditertiary acetalene glycols, dialkyl dilauryl ammonium chloride and fatty acid alkali and alkaline earth metal salts.

Suitable anti-foam agents are silicones.

The active substance is so mixed, ground sieved and strained with the additives mentioned above that, in wettable powders, the solid particle size of from 0.02 to 0.04 and in pastes, of 0.03 is not exceeded. To produce emulsifiable concentrates and pastes, dispersing agents such as those given in the previous paragraphs, organic solvents and water are used. Examples of suitable solvents are the following: alcohols, benzene, xylenes, toluene, dimethyl sulphoxide, and mineral oil fractions boiling between 120° and 350°C. The solvents must be practically odorless, not phytotoxic, inert to the active substances and not readily inflammable.

Furthermore, the agents according to the invention can be applied in the form of solutions. For this purpose the active substances or several active substances of general formula II are dissolved in suitable organic solvents, mixtures of solvents or in water. Aliphatic and aromatic hydrocarbons, chlorinated derivatives thereof, slkyl naphthalenes and mineral oils singly or in admixture, can be used as organic solvents. The solutions contain the active substance in a concentration range from 1 to 20%.

In addition to fungicidal active substances, the agents described according to the invention can be mixed with other biocidally active substances or agents. Thus in order to broaden the activity spectrum the new agents may contain, for example, insecticides, fungicides, bactericides, fungistatics, bacteriostatics or nematocides, in addition to the cited active substance of the formula I. The agents according to the invention may also contain plant fertilisers, trace elements etc.

The active substances of formula I can, for example, be formulated as follows. The parts denote parts by weight.

Granules

The following substances are used to manufacture 5% granules:
5 parts of Compound No. 22, Table b),
0.25 parts of epichlorohydrin,
0.25 parts of cetyl polyglycol ether,
3.50 parts of polyethylene glycol ether,
91 parts of kaolin (particle size: 0.3–0.8 mm).

The active substance is mixed with epichlorohydrin and the mixture dissolved in 6 parts of acetone, then polyethylene glycol ether and cetyl polyglycol ether are added. The resulting solution is sprayed on kaolin and then evaporated in vacuo.

Wettable Powder

The following constituents are used to manufacture (a) a 50%, (b) a 25% and (c) a 10% wettable powder:
a. 50 parts of Compound No. 16, Table (b),
5 parts of sodium dibutylnaphthalene sulphonate,
3 parts of naphthalenesulphonic acid/phenolsulphonic acid/formaldehyde condensate (3:2:1),
20 parts of kaolin,
22 parts of Champagne chalk;
b. 25 parts of Compound No. 23, Table (b),
5 parts of oleylmethyltaurid-sodium-salt,
2.5 parts of naphthalenesulphonic acid/formaldehyde condensate,
0.5 part of carboxymethyl cellulose,
5 parts of neutral potassium-aluminium-silicate,
62 parts of kaolin;
c. 10 parts of Compound No. 41, Table (c),
3 parts of a mixture of the sodium salts of saturated fatty alcohol sulphates,
5 parts of naphthalenesulphonic acid/formaldehyde condensate,
82 parts of kaolin.

The indicated active substance is applied to the corresponding carriers (kaolin and chalk) and then these are mixed and ground, to yield wettable powders of excellent wettability and having an excellent capacity for forming suspensions. By diluting these wettable powders with water it is possible to obtain suspensions of every desired concentration of active substance.

Paste

The following substances are used to manufacture a 45% paste:
45 parts of Compound No. 17, Table b),
5 parts of sodium aluminium silicate,
14 parts of cetyl polyglycol ether with 8 mols of ethylene oxide,
1 part of oleyl polyglycol ether with 5 mols of ethylene oxide,
2 parts of spindle oil,
10 parts of polyethylene glycol,
23 parts of water.

The active substance is intimately mixed with the addition in appropriate devices and ground. A paste is obtained from which, by diluting it with water, is possible to manufacture suspensions of every desired concentration of active substance. The suspensions are suitable for treating vegetable plantations.

Emulsion Concentrate

To manufacture a 25% emulsion concentrate
25 parts of Compound No. 2, Table (a),
5 parts of a mixture of nonylphenolpolyoxy-ethoxyethylene and calcium, dodecylenesulphonate,
35 parts of 3,5,5-trimethyl-2-cyclohexan-1-one,
35 parts of dimethyl formamide,
are mixed together. This concentrate can be diluted with water to give emulsions in desired concentrations.

We claim:

1. A phosphorylacylamine compound of the formula

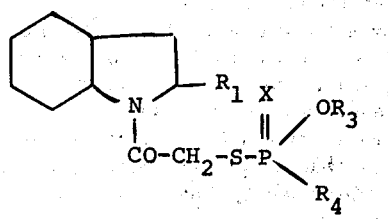

wherein $R_1$ is hydrogen or methyl, $R_3$ is alkyl of from 1 to 4 carbon atoms, $R_4$ is alkoxy of from 1 to 4 carbon atoms, and X is oxygen or sulphur.

2. A phosphorylacylamine according to Claim 1 in which $R_3$ is alkyl of from 1 to 3 carbon atoms and $R_4$ is alkoxy of from 1 to 3 carbon atoms.

3. 1-O,O-diisopropyl-thiophosphorylthio-acetyl)-octahydro-1H-indole according to claim 2 of the formula

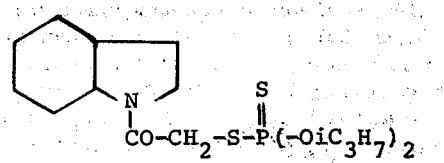

4. 1-(O,O-diethyl-thiophosphorylthio)-2-methyl-octahydro-1H-indole according to claim 2 of the formula

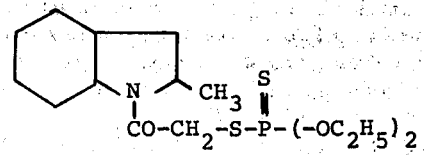

5. 1-(O,O-di-n-propyl-thisphosphorylthio-acetyl)-2-methyl-octahydro-IH-indole according to claim 2 of the formula

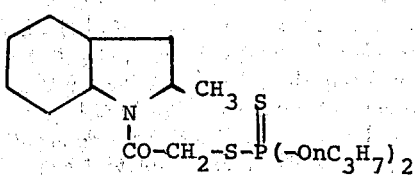

* * * * *